United States Patent [19]

Halczenko et al.

[11] Patent Number: 4,837,205
[45] Date of Patent: Jun. 6, 1989

[54] PRODRUGS OF ANTIHYPERCHOLESTEROLEMIC COMPOUNDS

[75] Inventors: Wasyl Halczenko, Hatfield; George Hartman; Steven M. Pitzenberger, both of Lansdale, all of Pa.

[73] Assignee: Merck & Co., Inc., Rahway, N.J.

[21] Appl. No.: 902,894

[22] Filed: Sep. 2, 1986

[51] Int. Cl.$^4$ .................. A61K 31/70; A61K 31/335; C07D 319/04
[52] U.S. Cl. ...................... 514/25; 514/452; 549/375; 549/229; 536/4.1
[58] Field of Search .................. 514/452, 25; 549/375, 549/229; 536/4.1

[56] References Cited

U.S. PATENT DOCUMENTS 4,375,475 3/1983 Willard et al. ...................... 549/292

FOREIGN PATENT DOCUMENTS 58-188873 11/1983 Japan ..................... 549/375

*Primary Examiner*—Nicky Chan
*Attorney, Agent, or Firm*—Melvin Winokur; Joseph F. DiPrima

[57] ABSTRACT

Prodrugs of 3-hydroxy-3-methylglutarylcoenzyme A (HMG-CoA) reductase inhibitors which are useful as antihypercholesterolemic agents and are represented by the following general structural formula (I):

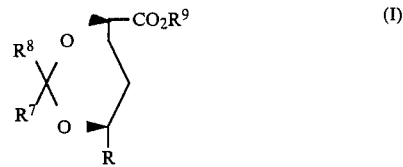

are disclosed.

13 Claims, No Drawings

PRODRUGS OF ANTIHYPERCHOLESTEROLEMIC COMPOUNDS

BACKGROUND OF THE INVENTION hypercholesterolemia is known to be one of the prime risk factors for ischemic cardiovascular disease, such as arteriosclerosis. To date, there is still no effective antihypercholesterolemic agent commercially available that has found wide patient acceptance. The bile acid sequestrants seem to be moderately effective but they must be consumed in large quantities, i.e. several grams at a time and they are not very palatable.

There are agents known, however, that are very active antihypercholesterolemic agents that function by limiting cholesterol biosynthesis by inhibiting the enzyme, HMG-CoA reductase. These agents include the natural fermentation products compactin and mevinolin and a variety of semisynthetic and totally synthetic analogs thereof.

The naturally occurring compounds and their semisynthetic analogs have the following general structural formulae:

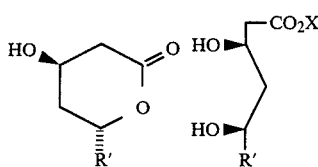

wherein

X is hydrogen, $C_{1-5}$alkyl or $C_{1-5}$alkyl substituted with a member of the group consisting of phenyl, dimethylamino or acetylamino;
R' is

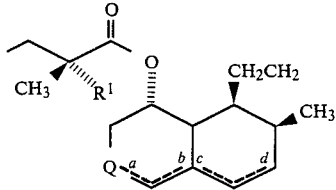

wherein
Q is

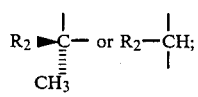

$R_2$ is hydrogen or hydroxy;
$R_1$ is hydrogen or methyl; and
a, b, c and d are single bonds, one of a, b, c and d is a double bond or a and c or b and d are double bonds provided that when a is a double bond, Q is

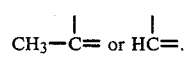

The totally synthetic antihypercholesterolemic compounds are disclosed in U.S. Pat. No. 4,375,475 and have the following general structural formulae:

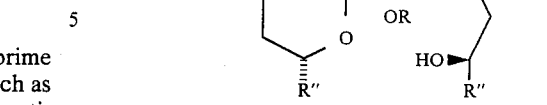

wherein R'' is:

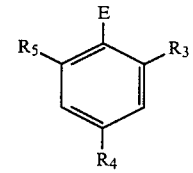

wherein
E is $-CH_2-$, $-CH_2CH_2-$ or $-CH=CH-$;
$R_3$ and $R_4$ are independently $C_{1-3}$alkyl, fluoro, bromo or chloro; and
$R_5$ is phenyl, benzyloxy, substituted phenyl or substituted benzyloxy in which the phenyl group in each case is substituted with one or more substituents selected from $C_{1-3}$alkyl, fluoro, bromo or chloro.

SUMMARY OF THE INVENTION

This invention relates to novel compounds which are prodrugs of known HMG-CoA reductase inhibitors and which are bioconverted following systemic administration to useful antihypercholesterolemic agents. Specifically, the compounds of this invention include acetal and ketal derivatives of the dihydroxy acid form of compactin, mevinolin, CS514, the dihydro and tetrahydro analogs thereof and the totally synthetic HMG-CoA reductase inhibitors. Additionally, pharmaceutical compositions of these prodrugs, as the sole therapeutic agent, and in combination with bile acid sequestrants are disclosed.

DETAILED DESCRIPTION OF THE INVENTION

The specific prodrugs of this invention are the compounds represented by the following general structural formula (I):

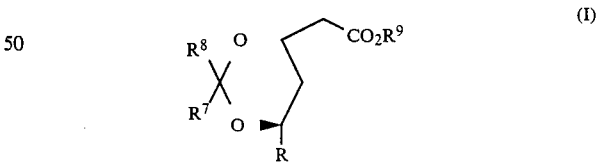

wherein:
R is selected from a group consisting of:

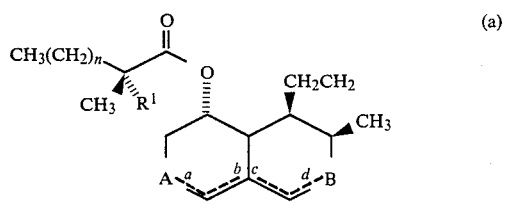

wherein:

n is 1 to 5;
$R^1$ is hydrogen or methyl;
A is $$R^2\!-\!\underset{CH_3}{\overset{|}{C}}\!-\ \text{or}\ R^2\!-\!\overset{|}{\underset{|}{CH}},$$

in which $R^2$ is hydrogen or hydroxyl;
B is $$-\overset{|}{C}HR^3,$$

in which $R^3$ is hydrogen or hydroxyl;
a, b, c and d represent single bonds, one of a, b, c and d represents a double bond or both a and c or both b and d represent double bonds, provided that when a is a double bond, A is $$\underset{CH_3}{\overset{|}{\diagup}}\overset{|}{C}=\ \text{or}\ \overset{|}{CH}=$$

and when d is a double bond, B is $$=\overset{|}{CH};$$

or $$\text{(b)}\quad R^6\!\!\underset{R^5}{\overset{E}{\diagdown\!\!\diagdown}}\!\!R^4$$

wherein:
E is —CH$_2$——, —CH$_2$CH$_2$— or —CH=CH—;
$R^4$ and $R^5$ are independently $C_{1-3}$alkyl, fluoro, bromo or chloro; and
$R^6$ is phenyl, benzyloxy, substituted phenyl or substituted benzyloxy in which the phenyl group in each case is substituted with one or more substituents selected from $C_{1-3}$alkyl, fluoro, bromo or chloro;
$R^7$ is hydrogen or $C_{1-6}$ alkyl;
$R^8$ is $C_{1-6}$ alkyl; and
$R^9$ is $C_{1-6}$alkyl, $C_{1-6}$acyloxy-$C_{1-6}$alkyl, $C_{1-6}$alkoxycarbonyloxy-$C_{1-6}$alkyl or a group selected from
(1) (5-(1,1-dimethylethyl)-2-oxo-1,3-dioxol-4-yl)methyl; or
(2) 2-(β-D-galactosidyl)ethyl.

One embodiment of this invention are the compounds of the formulae (I) wherein R is the group (b). Illustrative of this embodiment are compounds wherein E is —CH=CH—; $R^4$ and $R^5$ are independently $C_{1-3}$alkyl and $R^6$ is substituted phenyl. More specifically, group (b) is:

Exemplifying this embodiment are the class of compounds wherein $R^9$ is $C_{1-6}$alkyl and specifically, ethyl 6(S)-E-[2-[(4'-fluoro-3,3',5-trimethyl)[1,1'-biphenyl]-2-yl)ethenyl]-2,2-dimethyl-1,3-dioxane-4(R)-acetate.

A second class of compounds exemplifying this embodiment contain those compounds wherein $R^9$ is $C_{1-6}$acyloxy-$C_{1-6}$alkyl and specifically (2,2-dimethyl-1-oxopropoxy)methyl 6-(S)-E-[2-[(4'-fluoro-3,3',5-trimethyl)[1,1'-biphenyl]-2-yl]ethenyl]-2,2-dimethyl-1,3-dioxane-4(R)-acetate.

A third class of compounds exemplifying this embodiment contain those compounds wherein $R^9$ is $C_{1-6}$alkoxyacyloxy-$C_{1-6}$alkyl, such as [[(1,1-dimethylethoxy)carbonyl]oxy]methyl 6(S)-E-[2-[(4'-fluoro-3,3',5-trimethyl)[1,1'-biphenyl]-2-yl]ethenyl]]-2,2-dimethyl-1,3-dioxane-4(R)-acetate.

A fourth class of compounds exemplifying this embodiment contain those compounds wherein $R^9$ is [5-(1,1-dimethylethyl)-2-oxo-1,3-dioxol-4-yl]-methyl, such as [5-(1,1-dimethylethyl)-2-oxo-1,3-dioxol-4-yl]]-methyl 6(S)-E-[2-[(4'-fluoro-3,3',5-trimethyl[1,1'-biphenyl]-2-yl)ethenyl]-2,2-dimethyl-1,3-dioxane-4(R)-acetate.

Another class of compounds exemplifying this embodiment contain those compounds wherein $R^9$ is 2-(β-D-galactosidyl)ethyl, such as 2-(β-D-galactosidyl)ethyl 6(S)-E-[2-[(4'-fluoro-3,3',5-trimethyl)[1,1'-biphenyl]-2-yl]ethenyl]-2,2-dimethyl-1,3-dioxane-4(R)-acetate.

A second embodiment of this invention are the compounds of the formula (I) wherein R is the group (a).

The compounds of this invention are conveniently prepared by either (1) an acetalization or ketalization of the ring opened dihydroxy ester form of known HMG-CoA reductase inhibitors; or (2) the acetalization or ketalization of the ring opened dihydroxy acid form of known HMG-CoA reductase inhibitors followed by esterification according to the following synthetic pathway:

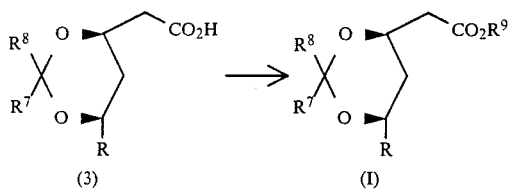

The compounds of the formula (1) are known in the art. When R is the group (a), the compounds of the formula (1) are the ring opened dihydroxy acid form of compactin, mevinolin, CS514 and their dihydro and tetrahydro analogs which are readily available or may be prepared according to the fermentation procedures disclosed in U.S. Pat. Nos. 3,983,140; 4,049,495; 4,231,938; 4,294,846 and 4,517,373 and the hydrogenation procedures disclosed in U.S. Pat. No. 4,351,844. When R is the group (b), the compounds of the formula (1) are readily available by utilizing the procedures described in U.S. Pat. No. 4,375,475.

According to the first reaction sequence, the compounds of the formula (1) are neutralized with a primary amine, such as α-methylbenzylamine, to form the ammonium salt which is then treated with the appropriate organohalide, $R^9$hal, wherein hal is bromo or chloro, to afford the compounds of the formula (2). The compounds of the formula (2) are then treated with the appropriate aldehyde, ketone or enol ether thereof in the presence of a catalytic amount of an acid, such as p-toluenesulfonic acid, to give the compounds of the formula (I). The sequence of the reactions may be reversed so that the acetal or ketal of the formula (3) is prepared and then esterified to obtain the compounds of the formula (I).

The compounds of this invention are useful as prodrugs of antihypercholesterolemic agents for the treatment of arteriosclerosis, hyperlipidemia, familial hypercholesterolemia and the like diseases in humans. They may be administered orally in the form of a capsule, a tablet, or the like. Doses may be varied, depending on the age, severity, body weight and other conditions of human patients but daily dosage for adults is within a range of from about 20 mg to 2000 mg (preferably 20 to 100 mg) which may be given in two to four divided doses. Higher doses may be favorably employed as required.

The compounds of this invention may also be coadministered with pharmaceutically acceptable nontoxic cationic polymers capable of binding bile acids in a non-reabsorbable form in the gastrointestinal tract. Examples of such polymers include cholestryamine, colestipol and poly[methyl-(3-trimethylaminopropyl)iminotrimethylene dihalide]. The relative amounts of the compounds of this invention and these polymers is between 1:100 and 1:15,000.

The ability of the compounds of this invention to act as prodrugs of antihypercholesterolemic agents is demonstrated in a standard in vivo pharmacological assay in dogs.

Eight male beagle dogs weighing from 7.2–12.9 kilograms approximately 4–5 years old were fed a low cholesterol, semi-synthetic diet once a day in the morning in sufficient quantity to maintain a constant body weight. The animals were trained to consume their entire ration each day. Cholestyramine, 12 g, was administered daily in the diet. This amount routinely resulted in an average reduction in plasma total cholesterol of approximately 35%. Dogs were bled twice a week from the jugular vein and plasma cholesterol was determined after extraction and saponification by a colorimetric procedure (Liebermann Burchard). After the establishment of pretreatment plasma cholesterol levels, one or more dogs were treated with daily doses of test compound mixed directly into the diet for 14 days.

Representative of the pharmacological activity of the compounds of this invention tabulated below are a number of compounds and the percentage decrease in cholesterol levels in dogs at specified dosages after 14 days of treatment.

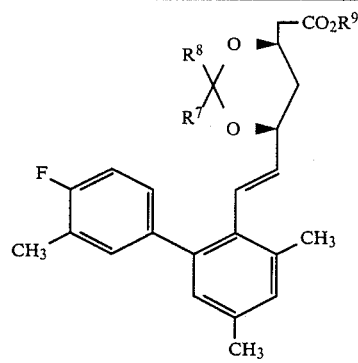

| Compounds | | | Dosage | Percent Reduction in Plasma |
|---|---|---|---|---|
| $R^7$ | $R^8$ | $R^9$ | (mg/kg/day) | Cholesterol |
| Me | Me | —$CH_2CH_3$ | 8 | 32 |
| Me | Me | —$CH_2OCC(CH_3)_3$ (O=) | 8 | 27 |

Included within the scope of this invention is the method of treating arteriosclerosis, familial hypercholesterolemia or hyperlipidemia which comprises administering to a subject in need of such of the compounds of formula (I) or pharmaceutical compositions thereof.

The following examples illustrate the preparation of the compounds of the formula (I) and their incorporation into pharmaceutical compositions and as such are not to be considered as limiting the invention set forth in the claims appended hereto.

EXAMPLE 1

Preparation of Ethyl 6(S)-E-[2-[(4'-fluoro-3,3',5-trimethyl)[1,1'-biphenyl]-2-yl]-2,2-dimethyl-1,3-dioxane-4(R)-acetate To 2.0 g (5 mmol) ethyl 7-[(4'-fluoro-3,3',5-trimetyl)[1,1'-biphenyl]-2-yl]-3(R),5(S)-dihydroxy-6(E)-heptenoate and 0.72 g (10 mmol) 2-methoxypropene dissolved in 25 ml DMF was added 10 mg of p-toluenesulfonic acid monohydrate at room temperature. After stirring for 16 hours, the reaction mixture was taken up in 125 ml diethyl ether and washed with 3×25 ml portions of water, 25 ml saturated sodium bicarbonate solution, 25 ml $H_2O$, brine and dried. The solvent was removed in vacuo to give an oil that was purified by flash chromatography on silica gel eluting with hexane:$Et_2O$ (4:1). Solvent removal left an oil which was triturated to give the above titled compound as a white solid, m.p. 76°–78°.

Anal. Calc'd for $C_{27}H_{33}FO_4$: C, 73.61; H, 7.55; Found: C, 73.67; H, 7.87.

EXAMPLE 2

Preparation of (2,2Dimethyl-1-oxopropoxy)methyl 6(S)-E-[2[(4'-fluoro-3,3',5-trimethyl)[1,1'-biphenyl]-2-yl]ethyl]-2,2-dimethyl-1,3-dioxane-4(R)-acetate (a) Pivaloyloxymethyl E-7-(4'-fluoro-3,3',5-trimethyl[1,1'-biphenyl]-2-yl)-3(R),5(S)-dihydroxyhept-6-enoate (2a)

To 29.62 g (60 mmol) of the α-methylbenzylammonium salt of 7-[(4'-fluoro-3,3',5-trimethyl)[1,1-biphenyl]-2-yl]-3(R),5(S)-dihydroxy-6(E)-heptenoic acid in 165 ml DMF was added 18.07 g (120 mmol) chloromethyl pivalate, 0.8 g potassium carbonate and 4.8 ml of 10% aqueous potassium iodide and the resulting mixture stirred at room temperature for 18 hours. The reaction mixture was diluted with 400 ml diethyl ether and this was washed with 3×200 ml portions H$_2$O, 75 ml saturated NaHCO$_3$ solution, brine and dried. Solvent removal in vacuo gave an oil that was purified by Flash chromatography on silica gel eluting with 5% isopropanol/hexane to give an oil. This was triturated with hexane to give pure desired product as a white solid, m.p. 97°–98°.

(b) (2,2-Dimethyl-1-oxopropoxy)methyl 6(S)-[2-[(4'-fluoro-3,3',5-trimethyl)[1,1'-biphenyl]-2-yl]-ethenyl]-2,2-dimethyl-1,3-dioxane-4(R)-acetate To 1.46 g (3.0 mmol) compound 2a in 15 ml DMF was added 0.43 g (6.0 mmol) 2-methoxypropene and 10 mg p-toluenesulfonic acid monohydrate with stirring. After 18 hours at room temperature the reaction mixture was taken up in 75 ml Et$_2$O and washed successively with 3×15 ml H$_2$O, 15 ml saturated NaHCO$_3$ solution, 15 ml H$_2$O, brine and dried. Solvent removal in vacuo gave an oil which was purified by flash chromatography on silica gel eluting with 25% isopropanol/hexane to give a solid. This was recrystallized from hexane to afford the above titled compound, m.p. 120°–121°.

Anal. Calc'd for $C_{31}H_{39}FO_6$: C, 70.70; H, 7.46; Found: C, 70.62; H, 7.53.

EXAMPLE 3

Preparation of [[(1,1-Dimethylethoxy)carbonyl]oxy]methyl 6(S)-E-[2-[(4'-fluoro-3,3',5-trimethyl)[1,1'-biphenyl]-2-yl]ethenyl]-2,2-dimethyl-1,3-dioxane-4(R)-acetate (a) ([Dimethylethoxy)carbonyl]oxy)methyl E-7-[(4'-fluoro-3,3',5-trimethyl) [1,1'-biphenyl]-2-yl]-3(R),5(S)-dihydroxyhept-6-enoate (3a)

To 0.79 g (2 mmol) of the α-methylbenzylammonium salt of 7-[4'-fluoro-3,3',5-trimethyl)[1,1-biphenyl]-2-yl]-3(R),5(S)-dihydroxy-6(E)-heptenoic acid in 6 ml DMF at room temperature was added 0.67 g (4 mmol), chloromethyl t-butylcarbonate, 60 mg sodium iodide and 20 mg potassium carbonate with stirring. After 24 hours at room temperature the reaction mixture was poured into 25 ml H$_2$O and this was extracted with 5×30 portions of diethyl ether. The combined organic extracts were washed with 2×25 ml portions of H$_2$O, brine and dried. Solvent removal in vacuo gave a yellow oil that was purified by flash chromatography on silica gel eluting with 5% isopropanol/hexane to give a white residue. This was triturated with ;b 5% isopropanol/hexane to give the desired product as a white solid, m.p. 103°–104°.

(b) [[(1,1-Dimethylethoxy)carbonyl]oxy]methyl 6(S)-E-[2-[(4'-fluoro-3,3',5-trimethyl)[1,1'-biphenyl]]-2-yl]ethenyl]-2,2-dimethyl-1,3-dioxane-4(R)-acetate To 1.02 g (2 mmol) compound 3a in 5 ml DMF at room temperature was added 0.288 g (4 mmol) 2-methoxypropene and 20 mg p-toluenesulfonic acid monohydrate and the resulting solution was stirred overnight. This was poured into 75 ml cold H$_2$O and extracted with 4×75 ml portions of diethyl ether. The combined organic extracts were washed with 3×50 ml H$_2$O, 2×25 ml portions of saturated NaHCO$_3$ solution, brine, and dried. The solvent was removed in vacuo to give a yellow oil that was purified by flash chromatography on silica gel eluting with hexane:diethyl ether (5:1) to give an oil. This was triturated with hexane to provide the above titled compound as a white solid, m.p. 98°–100°.

Anal. Calc'd for $C_{31}H_{39}FO_7$: C, 68.61; H, 7.24; Found: C, 68.72; H, 7.45.

EXAMPLE 4

Preparation of [5-(1,1Dimethylethyl)-2-oxo-1,3-dioxol-4-yl]metyl 6(S)-E-[2-[(4'-fluoro-3,3',5-trimethyl)[1,1'-biphenyl]-2-yl]ethenyl]-2,2-dimethyl-1,3-dioxane-4(R)-acetate (a) (5-[(1,1-Dimethylethyl)-2-oxo-1,3-dioxol-4-yl])methyl E-7-(4'-fluoro-3,3',5-trimethyl-[1,1'-biphenyl]-2-yl)-3(R),5(S)-dihydroxyhept-6-enoate (4a)

To 4.94 g (10 mmol) α-methylbenzylammonium salt of 7-[(4'-fluoro-3,3',5-trimethyl)[1,1-biphenyl]-2-yl]-3(R),5(S)-dihydroxy-6(E)-heptenoic acid in 35 ml DMF at room temperature was added 2.59 g (11 mmol) 4-bromomethyl-5-tert-butyl-2-oxo-1,3-dioxolene dropwise followed by 100 mg of potassium carbonate. This suspension was stirred at room temperature for 16 hours. The solvent was removed in vacuo (<50° C.) and the residue was taken up in 350 ml diethyl ether. This was washed with 4×75 ml portions of H$_2$O, brine and dried. The solvent was removed in vacuo to give an oil which was purified by flash chromatography on silica gel eluting with 8% isopropyl/hexane to give the desired product as a clear oil.

(b) (5-[(1,1-Dimethylethyl)-2-oxo-1,3-dioxol-4-yl]-methyl 6(S)-E-[2-(4'-fluoro-3,3',5-trimethyl-[1,1'-biphenyl]-2-yl)ethenyl]-2,2-dimethyl-1,3-dioxane-4(R)-acetate To 1.6 g (3 mmol) compound 4a in 5 ml DMF at room temperature was added 0.433 g (6 mmol) 2-methoxypropene and 20 mg p-toluenesulfonic acid monohydrate with stirring. After 24 hours the reaction mixture was poured into 75 ml cold H$_2$O and extracted with 4×75 ml portions of diethyl ether. The combined organic extracts were washed with 3×50 ml portions of H$_2$O, 2×25 ml portions of saturated NaHCO$_3$ solution, 50 ml H$_2$O, brine and dried. Solvent removal in vacuo gave a yellow oil that was purified by flash chromatography on silica gel eluting with hexane:diethyl ether (3:1) to give a clear oil. This was triturated with hexane to give the above titled compound as a white solid, m.p. 88°-90°.

Anal. Calc'd for $C_{33}H_{39}FO_7$: C, 69.94; H, 6.94; Found: C, 70.06; H, 7.5.

EXAMPLE 5

Preparation of 2-($\beta$-D-galactosidyl)ethyl 6(S)-E-[2-[(4'-fluoro-3,3',5-trimethyl)[1,1'-biphenyl]-2-yl]-2,2-dimethyl-1,3-dioxane-4(R)-acetate (a) 6(S)-E-[2-(4'-fluoro-3,3',5-trimethyl[1,1'-biphenyl]-2-yl)ethenyl]-2,2-dimethyl-1,3-dioxane-4(R)-acetic acid (5a)

To 0.2 g (0.5 mmol) $\alpha$-methylbenzylammonium salt of 7-[(4'-fluoro-3,3',5-trimethyl)[1,1-biphenyl]-2-yl]-3(R),5(S)-dihydroxy-6(E)-heptenoic acid in 5 ml DMF was added 0.072 g (1.0 mmol) 2-methoxypropene and 2 mg p-toluenesulfonic acid monohydrate at room temperature and the resulting solution stirred overnight at room temperature. After 18 hours the reaction mixture was diluted with 15 ml diethyl ether and washed successively with 3×3 ml portions of H$_2$O, 1 ml saturated NaHCO$_3$ solution, 3 ml H$_2$O, brine and dried. Solvent removal gave a gum that was recrystallized from hexane to give the desired product as a solid.

(b) 2-($\beta$-D-Galactosidyl)ethyl 6(S)-E-[2-(4'-fluoro-3,3',5-trimethyl[1,1'-biphenyl]-2-yl)ethenyl]-2,2-dimethyl-1,3-dioxane-4(R)-acetate To 1.03 g (2.5 mmol) 2-bromoethyl-$\beta$-D-galactopyranoside [prepared by the method of G. Magmusson et al., *Carbohydr. Res.*, 125, 237 (1984)] dissolved in 10 ml DMF was added 2.5 ml of a 1N NaOH solution (slight exotherm) and this was stirred for 1 hour. Then, 0.035 g (0.25 mmol) K$_2$Co$_3$ was added followed by 0.2 ml of a 10% NaI solution and a solution of 0.86 g (3.0 mmol) compound 5a in 5 ml DMF. The resulting mixture was stirred at room temperature for 3 days.

The solvent was removed in vacuo and the residue purified by flash chromatography on silica gel eluting with 10% MeOH/CHCl$_3$ to give the above titled compound as a white solid, m.p. 71°-73°.

Anal. Calc'd for $C_{33}H_{43}FO_{10}.2H_2O$: C, 60.54; H, 7.24 Found: C, 60.61; H, 7.02.

EXAMPLES 6–14

The following compounds in Tables I and II are prepared according to the general procedures of Examples 1 and 2 utilizing the appropriate starting materials.

TABLE I

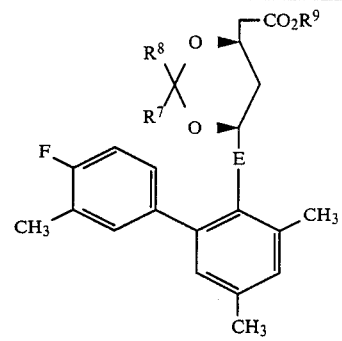

| Compound No. | E | $R^7$ | $R^8$ | $R^9$ |
|---|---|---|---|---|
| 6 | —CH$_2$CH$_2$— | Et | H | Me |
| 7 | —CH=CH— | nPr | Me | —(CH$_2$)$_3$OCCH$_3$ (O) |
| 8 | —CH$_2$— | sec-Bu | Et | —(CH$_2$)$_2$OCCH$_3$ (O) |
| 9 | —CH=CH— | n-amyl | H | nBu |

TABLE II

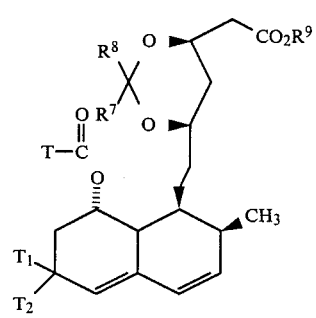

| Compound No. | T | $T^1$ | $T^2$ | $R^7$ | $R^8$ | $R^9$ |
|---|---|---|---|---|---|---|
| 10 | isobutyl (CH$_2$CH(CH$_3$)) | H | CH$_3$ | CH$_3$ | CH$_3$ | —CH$_2$CH$_3$ |
| 11 | tert-butyl (C(CH$_3$)$_3$) | H | CH$_3$ | CH$_3$ | CH$_3$ | —CH$_2$OCC(CH$_3$)$_3$ (O) |
| 12 | isobutyl (CH$_2$CH(CH$_3$)) | OH | CH$_3$ | CH$_3$ | CH$_3$ | —CH$_2$OCOC(CH$_3$)$_3$ (O) |

TABLE II-continued

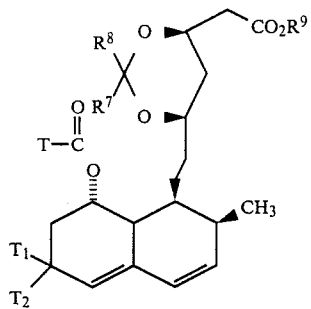

| Compound No. | T | T¹ | T² | R⁷ | R⁸ | R⁹ |
|---|---|---|---|---|---|---|
| 13 | 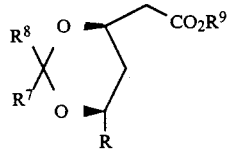 | H | H | $CH_3$ | $CH_3$ | —$CH_2$— (5-(1,1-dimethylethyl)-2-oxo-1,3-dioxol-4-yl)methyl group with $C(CH_3)_3$ |
| 14 | 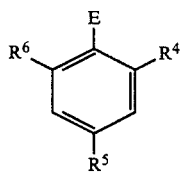 | H | $CH_3$ | $CH_3$ | $CH_3$ | —$CH_2CH_2O$— galactosidyl group |

EXAMPLE 15

As a specific embodiment of a composition of this invention, 20 mg of the compound of Example 1 is formulated with sufficient finely divided lactose to provide a total amount of 580 to 590 mg to fill a size 0 hard gelatin capsule.

What is claimed is:

1. A compound represented by the general structural formula (I):

(I)

[structure with $R^8$, $R^7$, O, O, $CO_2R^9$, R]

wherein:
R is

[structure with $R^6$, E, $R^4$, $R^5$]

wherein:
E is —$CH_2$—, —$CH_2CH_2$— or —CH=CH—;
$R^4$ and $R^5$ are independently $C_{1-3}$alkyl, fluoro, bromo or chloro; and
$R^6$ is phenyl, benzyloxy, substituted phenyl or substituted benzyloxy in which the phenyl group in each case is substituted with one or more substituents selected from $C_{1-3}$alkyl, fluoro, bromo or chloro;
$R^7$ is hydrogen or $C_{1-6}$alkyl;
$R^8$ is $C_{1-6}$alkyl; and
$R^9$ $C_{1-6}$alkyl, $C_{1-6}$alkanyloxy-$C_{1-6}$alkyl, $C_{1-6}$alkoxycarbonyloxy-$C_{1-6}$alkyl or a group selected from
(1) (5-(1,1-dimethylethyl)-2-oxo-1,3-dioxol-4-yl)methyl; or
(2) 2-(β-D-galactosidyl)ethyl.

2. A compound of claim 2 wherein E is —CH=CH—.

3. A compound of claim 2 wherein: $R^4$ and $R^5$ independently are $C_{1-3}$alkyl; and $R^6$ is a substituted phenyl.

4. A compound of claim 3 wherein R is:

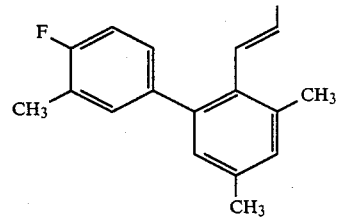

5. A compound of claim 4 wherein $R^9$ is $C_{1-6}$alkyl.

6. A compound of claim 5 which is ethyl 6(S)-E-[2-[(4'-fluoro-3,3',5-trimethyl)-[1,1'-biphenyl]-2-yl]ethenyl]-2,2-dimethyl-1,3-dioxane-4(R)-acetate.

7. A compound of claim 4 wherein $R^9$ is $C_{1-6}$-alkanoyloxy-$C_{1-6}$alkyl.

8. A compound of claim 7 which is (2,2-dimethyl-1-oxopropoxy)methyl 6-(S)-E-[2-[(4'-fluoro-3,3',5-trimethyl)[1,1'-biphenyl]-2-yl]ethenyl]-2,2-dimethyl-1,3-dioxane-4(R)-acetate.

9. A compound of claim 4 wherein $R^9$ is $C_{1-6}$-alkoxycarbonyloxy-$C_{1-6}$alkyl.

10. A compound of claim 4 which is [5-(1,1-dimethylethyl)-2-oxo-1,3-dioxol-4-yl]-methyl 6(S)-E-[2-[(4'-fluoro-3',5-trimethyl)[1,1'-biphenyl]-2-yl]ethenyl]-2,2-dimethyl-1,3-dioxane-4(R)acetate.

11. A compound of claim 4 which is 2-($\beta$-D-galactosidyl)ethyl 6(S)-E-[2-[(4'-fluoro-3',3',5-trimethyl)[1,1'-biphenyl]-2-yl]ethenyl]-2,2-dimethyl-1,3-dioxane-4(R)acetate.

12. A hypocholesterolemic, hypolipidemic pharmaceutical composition comprising a nontoxic therapeutically effective amount of a compound of claim 1 and a pharmaceutically acceptable carrier.

13. A method of inhibiting cholesterol biosynthesis comprising the administration to a subject in need of such treatment a nontoxic therapeutically effective amount of a compound of claim 1.

* * * * *